United States Patent

Kim et al.

[11] Patent Number: 5,962,721
[45] Date of Patent: Oct. 5, 1999

[54] METHOD FOR PREPARATION OF CARBAMATES

[75] Inventors: Hoon Sik Kim; Sang Deuk Lee; Hyun-joo Lee; In-Seok Seo; Yong Jin Kim, all of Seoul, Rep. of Korea

[73] Assignee: Korea Institute of Science and Technology, Seoul, Rep. of Korea

[21] Appl. No.: 09/069,285

[22] Filed: Apr. 29, 1998

[30] Foreign Application Priority Data

May 13, 1997 [KR] Rep. of Korea .................. 97-18548

[51] Int. Cl.$^6$ .................................................. C07C 261/00
[52] U.S. Cl. ........................... 560/24; 560/25; 560/157; 560/158
[58] Field of Search ........................ 560/24, 25, 157, 560/158

[56] References Cited

U.S. PATENT DOCUMENTS

| | | |
|---|---|---|
| 3,338,956 | 8/1967 | Mountfield . |
| 3,461,149 | 8/1969 | Hardy et al. . |
| 3,660,458 | 5/1972 | Trotz et al. . |
| 3,979,427 | 9/1976 | Ottmann et al. . |
| 3,993,685 | 11/1976 | Zajacek et al. . |
| 4,134,880 | 1/1979 | Miyata et al. . |
| 4,178,455 | 12/1979 | Hirai et al. . |
| 4,186,269 | 1/1980 | Hirai et al. . |
| 4,219,661 | 8/1980 | Becker et al. . |
| 4,251,667 | 2/1981 | Kesling, Jr. .............. 560/24 |
| 4,262,130 | 4/1981 | Becker et al. . |
| 4,339,592 | 7/1982 | Becker et al. . |
| 4,474,978 | 10/1984 | Drent et al. . |
| 4,705,883 | 11/1987 | Grate et al. . |
| 4,976,679 | 12/1990 | Okawa et al. ............ 560/159 |

OTHER PUBLICATIONS

E.W. Stern et al. Carbonylation of Amines in the Presence of Palladium (II) Chloride , pp. 596–597, Journal of Organic Chemistry, vol. 31 (1966).

*Primary Examiner*—Brian M. Burn
*Assistant Examiner*—Brian J. Davis
*Attorney, Agent, or Firm*—Darby & Darby

[57] ABSTRACT

A method of preparing carbamates by reacting amine with alcohol and mixed gas of $CO/O_2$ in the presence of one or more catalyst selected from the group consisting of monovalent copper halide having the structural formula of $Cu[NCMe_4]X$, $K[CuX_2]$, $[CuX(S)]$ (wherein X=Cl, Br, or I; S=solvent) or monovalent copper compound having carbonyl group having the structural formula of $[Cu(CO)X_aL_b]_m Y_n$ (wherein, $X=CF_3CO_2$, Cl, $HB(pz)_3$ (wherein, pz=pyrazoyl,$C_3H_3N_2$), $LBF_2$, {$LBF_2$=difluoro-3,3'-(trimethylenedinitrilo)bis(2-butanone oximato)borate}; L=en, diene; $Y=BPh_4$, $AsF_6$; a,b=0,1; m=1–4; n=0,1).

8 Claims, No Drawings

METHOD FOR PREPARATION OF CARBAMATES

FIELD OF THE INVENTION

The present invention relates to a method of preparing carbamates having the following general formula and widely-used as raw material of agricultural chemicals or polymer, and more particularly, to a preparation method of carbamates by reacting amine with carbon monoxide and alcohol in the presence of monovalent copper compound as a catalyst.

$$R—(NHCO_2R')n$$

wherein R is selected from the group consisting of alkyl of 1 to 18 carbon atoms, cyclohexyl, phenyl, and benzyl; R' is selected from the group consisting of alkyl of 1 to 12 carbon atoms, cyclohexyl, phenyl, and benzyl; and n is 1 or 2.

DESCRIPTION OF THE PRIOR ART

Carbamate is prepared by the reacting isocyanate with alcohol, and the isocyanate is prepared from amine and phosgene, but this method not only employ to use fatally poisonous phosgene, but also produce a large amount of by-product of HCl, a pollutant. Further, the isocyanate, itself has a fatally-poisonous properties. In a way or another, these problems have greatly demanded a new method of preparing the carbamate without using the isocyanate.

There is a method of preparing carbamate without using isocyanate, wherein nitro compound or amine and carbon monoxide and alcohol are reacted at high temperature and high pressure in the presence of a catalyst.

A method of preparing isocyanate by reacting primary amine and CO in the presence of $PdCl_2$ is disclosed in Joumal of Organic Chemistry 31, 596 (1966). In this method, an equivalent amount of sodium hydrogen phosphate as that of the amine is used in order to remove the hydrogen chloride generated during reaction, but because it is not a catalyst reaction, it takes too much time for the reaction, and the conversion rate is low.

U.S. Pat. No. 3,461,149 and No. 3,979,427, disclose a preparation method of carbamates wherein chemical compounds of nitro, amine, azo, azoxy, etc. are used to prepare carbamate while employing a catalyst of palladium or rhodium or halides of palladium or rhodium. In order to increase the reaction rate, a cocatalyst such as metal halide for example, ferrous chloride is further used. However, this method also has problems, wherein a large amount of the cocatalyst used in the reaction must be separated after the reaction, and the equipment facility for the reaction is corroded by the cocatalyst.

There is a description in U.S. Pat. No. 4,178,455, that addition of a primary amine can promote the reaction rate and selectivity in preparing carbamates from aromatic nitro compounds, using platinum as a catalyst. However, this method has problems of separation and corrosion, too because it uses ferrous chloride as a redox active metal halide. In order to solve the corrosion problem, U.S. Pat. Nos. 4,219,661, 4,262,130 and 4,339,592 disclose a preparation method of carbamates from aromatic nitro compounds wherein a tertiary amine such as pyridine is added while the redox active metal halide is not employed. In this method, the element of VIII group such as palladium or platinum, etc. is used as catalyst. In the same reaction condition, U.S. Pat. Nos. 3,338,956, 3,993,685, and 4,705,883, a carbonyl compound of ruthenium or rhodium are used as catalyst, but a large amount of pyridine is required for the catalyst used in the reaction, and the pyridine is used as reaction solvent, too.

U.S. Pat. No. 4,474,978 teach the method of preparing carbamate by reacting a primary amine or urea with an aromatic nitro compound in the presence of CO and alcohol by using palladium catalyst coordinated with phosphine ligand, wherein the primary amine and urea are used in order to increase the reaction rate, and these are themselves turned into carbamate by the reaction thereby resulting in the gradual reduction of their amount during the reaction which in turn, reduces their influences on the reaction, too.

Japanese Unexamined Patent Publication No. 145601/1979 discloses the method of using palladium, palladium compound, and transition metal compound and employing a catalyst of palladium, palladium compound, and transition metal compound or a catalyst of palladium, ruthenium, rhodium, Lewis acid, and tertiary amine, but these methods have problems of low catalytic activity, the usage of expensive noble metals as catalyst, and the generation of large amount of by-products such as urea compound and N-alkyl amines.

In order to solve these problems, a method of reacting dialkylcarbonate with amine under relatively moderate reaction conditions was suggested. Japanese Examined Patent Publication No. 51-33095/1976 discloses a method of using uranyl acetate, and Lewis acid of antimony trichloride as a catalyst. However, because these catalysts not only catalyze the generation of carbamate activate, but also promote the alkylation of diesteramine carbonate, by-production of N-alkyl amine is increased. Further, although the uranium compound attributes the relatively good result but it has no merit in practical-wise because it is a radioactive element.

Japanese Unexamined Patent Publication No. 82361/1982 discloses a method of using neutral or basic compound of zinc, titanium, or zirconium as a catalyst. This method shows a good production yield of carbamates, but it takes too much time for the reaction and requires a high temperature, thus, this method is not industrially desirable.

Meanwhile, Japanese Unexamined Patent Publication No. 311452/1990 discloses a method of using a base as a catalyst, in which an alcohol of alkaline metal and alkaline earth-metal are employed. However, the base employed can be remained in the carbamate prepared by this method, and the remaining base must be removed by neutralization because otherwise, it may cause a polymerization or coloration during the conversion of carbamate into isocyanate.

According to Japanese Unexamined Patent Publication No. 275662/1991, ammonia or amine and diester carbonate are reacted by adding more than 1 mole % of water for the diester carbonate. However, the method does not include any example showing the efficiency for low-active aromatic amines. Further, it does not mention the method of preparing dicarbamate from diamine. In addition, this method requires to use excessive amount of amine, relative to diester carbonate with water, and besides, lots of labor is needed for the purification of the products.

Japanese Unexamined Patent Publication No. 25137/1994 teaches a method of using ion exchange resin as a solid catalyst. This method has advantages of using the solid catalyst and easy separation in the reaction system, but it takes long time for reaction due to the low catalytic activity. The selectivity for carbonate is also low in this method.

Japanese Unexamined Patent Publication No. 85854/1993, shows that when amine is used in an excessive amount relative to diester carbonate, the reaction proceeds rapidly without a catalyst and the carbamate can be obtained at a high yield and high selectivity. By this method, carbamate is prepared with a high yield at a short time even without using any other material except the raw material for the reaction. However, the method is not adequate to convert diamine into dicarbamate, and further, the process to prepare carbamate by using dialkyl carbonate costs very much because the production cost of the dialkyl carbonate is very expensive.

U.S. Pat. Nos. 3,660,458, 4,134,880, and 4,186,269 disclose the preparation method of urethane or isocyanate by the reaction of amine with ruthenium chloride as a catalyst. U.S. Pat. Nos. 3,461,149, and 3,979,427 teach the preparation method of carbamate by using heterogeneous catalyst system prepared by treating ruthenium carried on alumina with chloride such as $FeCl_2$ or $CF_3CCl_3$.

As described above, however, the related arts of preparing carbamates have many problems, that is, the preparation of carbamate from the reaction of low-active aromatic amine or the preparation of dicarbamate from diamine are not adequate methods in particular in an industrial application.

SUMMARY OF THE INVENTION

Therefore, it is an object of this invention to provide an improved method of preparing carbamates.

More particularly, it is another object of this invention to provide an improved method of preparing carbamates by reacting amine with alcohol and CO in the presence of monovalent copper compound as a catalyst.

DETAILED DESCRIPTION OF THE INVENTION

The present invention is directed to provide a new method of preparing carbamates, which substantially obviates the above mentioned prior art problems.

The present invention is based on the fact that the preparation method of carbamate by reacting amine with alcohol and CO as represented by reaction scheme (1) and the preparation method of dialkylcarbonate by reacting alcohol and CO as represented by reaction scheme (2) have closely related from each other and among the catalysts employed in the preparing method of dialkylcarbonate, a monovalent copper compound shows excellent catalytic activity in the synthesis of carbamates.

$$RNH_2 + CO + \tfrac{1}{2}O_2 + R'OH \rightarrow RNHCO_2R' + H_2O \quad (1)$$

$$CO + \tfrac{1}{2}O_2 + R'OH \rightarrow (R'O)_2CO + H_2O \quad (2)$$

$$RNH_2 + (R'O)_2CO \rightarrow RNHCO_2R' + R'OH \quad (3)$$

In addition, the present inventors found that even an aromatic amine with low reactivity and an amine compound having plural amine groups can be easily converted into carbamate by using monovalent copper catalyst. In addition, it is also advantageous because the use of expensive noble metal catalyst can be avoided due to the use of copper compound having high catalytic activity according to the present invention.

The present method is characterized by reacting amines with carbon monoxide and oxygen in the presence of monovalent copper compound as a catalyst in a liquid phase.

The reference of the present invention is made in detail now hereinafter. Alcohol used as raw material of the present invention has 1 to 12 carbon atoms, which there are for example ethanol, methanol, propanol, isopropanol, butanol, t-butanol, cyclohexanol, cyclodecanol, phenyl alcohol, etc., but preferably those having 1 to 4 carbon atoms are preferred in the aspect of reactivity. A primary amine or a secondary amine can be used as raw material of amine for the present invention. For example, linear or branched amine such as methyl amine, ethyl amine, isopropyl amine, butyl amine, isobutyl amine, hexyl amine, dodecyl amine, hexadecyl amine, octadecyl amine, etc., aromatic amine such as benzyl amine, phenylamine, etc., cycloalkyl amine such as cyclobutyl amine, cyclohexyl amine, etc., and amine compounds having more than one amine group such as 1,4-cyclohexandiamine, cycloalkyldiamine, etc.

As the catalyst of the present invention, at least one kind of monovalent copper compound can be selected from the group consisting of monovalent copper halide having the structural formula of $Cu[NCMe_4]X$, $K[CuX_2]$, $[CuX(S)]$ (wherein X=Cl, Br, or I; S=solvent) or monovalent copper compound having carbonyl group having the structural formula of $[Cu(CO)X_aL_b]_mY_n$ (wherein, $X=CF_3CO_2$, Cl, $HB(pz)_3$ (wherein, pz=pyrazoyl,$C_3H_3N_2$), $LBF_2$, $\{LBF_2 = $ difluoro-3,3'-(trimethylenedinitrilo)bis(2-butanone oximato)borate$\}$; L=en, diene; Y=$BPh_4$, $AsF_6$; a,b=0,1; m=1–4; n=0,1). The amount of catalyst used is 0.05 to 50 mole % of the amine, and preferably 0.5 to 10 mole %. If the amount of catalyst is less than 0.05 mole %, the reaction rate becomes too low, otherwise if it exceeds 50 mole %, it results in using too much amount of catalyst, which is not economical. The reaction temperature may be in the range of 80 to 250° C., and preferably, in the range of 120 to 200° C., considering the selectivity into carbamate and the reaction rate. The pressure range of the reaction is 30 to 200 atm., and an appropriate molar ratio of CO to $O_2$ ranges from 95:5 to 55:45, considering reaction activity and the explosiveness of the mixed gas.

Reference will now be made in detail to the preferred embodiments of the present invention, but the present invention is not confined to these examples and various modifications and variations will be provided without departing from the spirit or scope of the invention.

EXAMPLE 1

0.992 g (10 mmoles) of cyclohexyl amine, 25 cc of $CH_3OH$, and 36.9 mg (0.2mmole) of $[Cu(NCMe_4)]CI$ were charged into a 100 ml—high pressure reactor, and reacted under a pressure of 70 atm. at a temperature of 150° C. with mixed gas of $CO/O_2$ ($CO/O_2$=90/10) for 2 hours and then, the reactor was cooled down to a room temperature, and the reaction mixture was analyzed by a gas-liquid chromatography equipped with capillary column. As a result, the conversion rate of cyclohexyl amine was 87.3% and the yield of methyl cabamate was 85.5%.

The conversion rate of amine and the yield of methyl carbamate are calculated as follows.

$$\text{Conversion rate of amine} = \frac{\text{amount of amine reacted}}{\text{amount of amine used}} \times 100(\%)$$

$$\text{Yield of carbamate} = \frac{\text{amount of carbamate produced}}{\text{amount of amine used}} \times 100(\%)$$

EXAMPLES 2–13

Under the same conditions as described in Example 1, the reaction was carried out with various catalysts, and the results are shown in table 1.

TABLE 1

| Example No. | Catalyst | Conversion rate (%) | Production yield of carbamate (%) |
|---|---|---|---|
| 2 | $Cu[NCMe_4]Br$ | 84.4 | 87.1 |
| 3 | $Cu[NCMe_4]I$ | 91.0 | 89.6 |
| 4 | $K[CuCl_2]$ | 83.3 | 80.6 |
| 5 | $K[CuI_2]$ | 87.4 | 82.4 |
| 6 | $[(CuCl)(TFH)]_n$ | 79.4 | 79.9 |
| 7 | $[Cu(CO)Br]_n$ | 81.9 | 82.2 |
| 8 | $[Cu(en)(CO)]BPh_4$ | 73.5 | 71.3 |
| 9 | $[Cu(LBF_2)(CO)]$ | 77.4 | 73.8 |
| 10 | $[Cu(HB(pz)_3)(CO)]$ | 78.5 | 75.6 |
| 11 | $[Cu(diene)(CO)](BPh_4)$ | 80.1 | 76.2 |
| 12 | $[Cu(CF_3CO_2)CO]$ | 82.3 | 78.3 |
| 13 | $[Cu(CO)]AsF_6$ | 78.2 | 77.9 |

EXAMPLES 14–20

Under the same conditions as described in Example 1, the reaction was carried out while changing the amount of catalyst [Cu(NCMe$_4$)]Cl, and the results are shown in table 2.

TABLE 2

| Example No. | Amount of catalyst (mole %) | Conversion rate (%) | Production yield of carbamate (%) |
|---|---|---|---|
| 14 | 0.05 | 69.8 | 68.9 |
| 15 | 0.1 | 74.5 | 73.4 |
| 16 | 0.5 | 91.4 | 90.8 |
| 17 | 2.0 | 93.2 | 91.7 |
| 18 | 5.0 | 96.8 | 95.9 |
| 19 | 20.0 | 98.4 | 96.9 |
| 20 | 50.0 | 98.8 | 97.0 |

EXAMPLES 21–25

Under the same conditions as described in Example 1, the reaction was carried out while changing temperature, pressure, and CO/O$_2$ molar ratio, and the results are shown in table 3.

TABLE 3

| Example No. | Temp. (°C.) | pressure (atm.) | CO/O$_2$ molar ratio | Conversion rate (%) | Yield(%) |
|---|---|---|---|---|---|
| 21 | 80 | 200 | 55/45 | 23.1 | 23.0 |
| 22 | 120 | 100 | 70/30 | 46.9 | 45.9 |
| 23 | 150 | 60 | 80/20 | 88.5 | 86.1 |
| 24 | 200 | 50 | 90/10 | 98.9 | 82.8 |
| 25 | 250 | 30 | 95/5 | 99.9 | 81.8 |

EXAMPLES 26–32

Under the same condition as in Example 1, the reaction was carried out while changing the kinds of raw materials amine and alcohol, and the results are shown in table 4.

TABLE 4

| Exam. No. | Amine | Alcohol | Conv. rate (%) | Yield of carbamate mono-carbamate | dicarbamate |
|---|---|---|---|---|---|
| 26 | cyclohexylamine | ethanol | 84.6 | 68.2 | — |
| 27 | aniline | methanol | 79.8 | 76.9 | — |
| 28 | O-phenyl-lendiamine | methanol | 81.1 | 32.6 | 46.9 |
| 29 | hexamethylen-diamine | t-butanol | 63.5 | 18.6 | 43.2 |
| 30 | n-butylamine | i-propanol | 93.4 | 90.9 | — |
| 31 | 1,3-clclohexan-diamine | n-hexanol | 61.9 | 20.2 | 39.6 |
| 32 | bis-(1,4-diphenyl)methyl-enediamine | methanol | 93.2 | 20.8 | 71.2 |

According to the present invention, aromatic amines of low reactivity and amine compounds having plural amine groups can be easily converted into carbamate by the use of monovalent copper catalysts. Further, it is another advantageous effect that the use of expensive noble metals can be avoided by employing such copper catalyst having high catalytic activity.

What is claimed is:

1. A method of preparing carbamates of the structural formula:

(wherein R is selected from the group consisting of alkyl of 1 to 18 carbon atoms, cyclohexyl, phenyl, or benzyl; R' is selected from the group consisting of alkyl of 1 to 12 carbon atoms, cyclohexyl, phenyl, or benzyl; and n is 1 or 2) by reacting amine with alcohol and mixed gas of CO/O$_2$ in the presence of one or more monovalent copper compounds as a catalyst, selected from the group consisting of a monovalent copper halide having the structural formula of Cu[NCMe$_4$]X, K[CuX$_2$], [CuX(S)] (wherein X=Cl, Br, or I; S=solvent) or a monovalent copper compound having a carbonyl group of the structural formula [Cu(CO)X$_a$L$_b$]$_m$Y$_n$ (wherein, X=CF$_3$CO$_2$, Cl, HB(pz)$_3$ (wherein, pz=pyrazoyl, C$_3$H$_3$N$_2$), LBF$_2$, {LBF$_2$=difluoro-3,3'-(trimethylenedinitrilo)bis(2-butanone oximato)borate}; L=en, diene; Y=BPh$_4$, AsF$_6$; a,b=0,1; m=1–4; n=0,1).

2. The method according to claim 1, wherein the amine used as raw material is selected from the group consisting of methyl amine, ethyl amine, isopropyl amine, butyl amine, isobutyl amine, hexyl amine, dodecyl amine, hexadecyl amine, octadecyl amine, benzyl amine, phenyl amine, cyclobutyl amine, cyclohexyl amine, 1,4-cyclohexandiamine, and cycloalkyldiamine.

3. The method according to claim 1, wherein alcohol used as raw material is an alcohol of 1 to 12 carbon atoms.

4. The method according to claim 3, wherein alcohol used as raw material is an alcohol of 1 to 4 carbon atoms.

5. The method according to claim 1, wherein the reaction temperature is 80 to 250° C. and the reaction pressure is 30 to 200 atm.

6. The method according to claim 1, wherein the monovalent copper compound is used in the amount of 0.05 to 50 mole % of the raw material amine.

7. The method according to claim 6, wherein the monovalent copper compound is used in the amount of 0.5 to 10 mole % of the raw material amine.

8. The method according to claim 1, wherein the molar ratio of CO to O$_2$ is 95:5 to 55:45.

* * * * *